United States Patent [19]

McCarthy et al.

[11] Patent Number: 5,677,476

[45] Date of Patent: Oct. 14, 1997

[54] SENSOR AND TRANSMITTER WITH MULTIPLE OUTPUTS

[75] Inventors: W. Patrick McCarthy, Indianapolis; Olaf F. Braster, Greenwood, both of Ind.

[73] Assignee: Endress + Hauser Conducta Gesellschaft fuer Mess- und Regeltechnik MBH & Co., Gerlingen, Germany

[21] Appl. No.: 597,207

[22] Filed: Feb. 6, 1996

[51] Int. Cl.$^6$ .............. G01R 19/00; H03K 17/60; G06F 1/00; G01W 1/00
[52] U.S. Cl. ............ 73/29.01; 73/335.02; 324/611; 324/669; 364/483; 364/571; 332/109
[58] Field of Search ............... 73/29.01, 335.02; 327/124, 408; 324/611, 669, 483, 571.03, 571.07; 332/109

[56] References Cited

U.S. PATENT DOCUMENTS

| | | | |
|---|---|---|---|
| 3,343,044 | 9/1967 | King, Jr. et al. | 317/146 |
| 3,477,279 | 11/1969 | Perlaky | 73/61.1 |
| 3,671,912 | 6/1972 | La Sota | 338/34 |
| 3,787,650 | 1/1974 | Lewis | 200/61.04 |
| 3,995,174 | 11/1976 | Zrudsky | 307/240 |
| 4,081,988 | 4/1978 | Change et al. | 73/4 R |
| 4,098,284 | 7/1978 | Yamada | 137/39 |
| 4,305,724 | 12/1981 | Micko | 23/232 E |
| 4,503,707 | 3/1985 | Rosa et al. | 73/336.5 |
| 4,590,789 | 5/1986 | Kunze | 73/1 G |
| 4,647,371 | 3/1987 | Schmitt et al. | 210/96.1 |
| 4,649,281 | 3/1987 | Schmitt et al. | 250/574 |
| 4,703,664 | 11/1987 | Kirkpatrick et al. | 73/866.5 |
| 4,768,378 | 9/1988 | Ando et al. | 73/336.5 |
| 4,788,488 | 11/1988 | Kramer et al. | 324/61 R |
| 4,821,557 | 4/1989 | Beeson, III | 73/3 |
| 4,926,340 | 5/1990 | Goetzinger et al. | 364/483 |
| 4,953,386 | 9/1990 | Pearman et al. | 73/3 |
| 5,003,810 | 4/1991 | Jepsou et al. | 73/3 |
| 5,065,625 | 11/1991 | Nakagawa et al. | 73/336.5 |
| 5,069,072 | 12/1991 | Taylor et al. | 73/75 |
| 5,189,902 | 3/1993 | Groeninger | 173/24.06 |
| 5,199,308 | 4/1993 | Lawhon et al. | 73/866.5 |
| 5,217,692 | 6/1993 | Rump et al. | 422/98 |
| 5,233,861 | 8/1993 | Gore et al. | 73/3 |
| 5,317,274 | 5/1994 | Nakagawa et al. | 324/678 |
| 5,361,048 | 11/1994 | Baum et al. | 332/109 |
| 5,502,659 | 3/1996 | Braster et al. | 364/571.01 |
| 5,531,097 | 7/1996 | Tsuchida et al. | 73/29.02 |

OTHER PUBLICATIONS

"Trace moisture, relative humidity, pressure, & oxygen measurement HygroTwin 2850", Technical Information TI 008M/03/ae, Endress + Hauser, Dec., 1992.

*Primary Examiner*—Hezron E. Williams
*Assistant Examiner*—J. David Wiggins
*Attorney, Agent, or Firm*—Bose McKinney & Evans

[57] ABSTRACT

A measuring transmitter assembly using the same lines for power input and for output signals and using a single power supply, has a first power input and signal output loop coupled to the power supply, a second power input and signal output loop coupled to the power supply, a first sensor for providing a first input signal in response to the value of a first parameter and a second sensor providing a second input signal in response to the value of a second parameter, and a controller coupled to the first and second sensors. The controller is also coupled to the first and second power input and signal output loops and provides a first output signal on the first power input and signal output loop in response to the first input signal and a second output signal on the second power input and signal output loop. The second output signal may be in response to only the second output signal or it may be in response to the first and second input signals. The assembly also has a digital isolator for electrically isolating the first power input and signal output loop from the second power input and signal output loop.

8 Claims, 8 Drawing Sheets

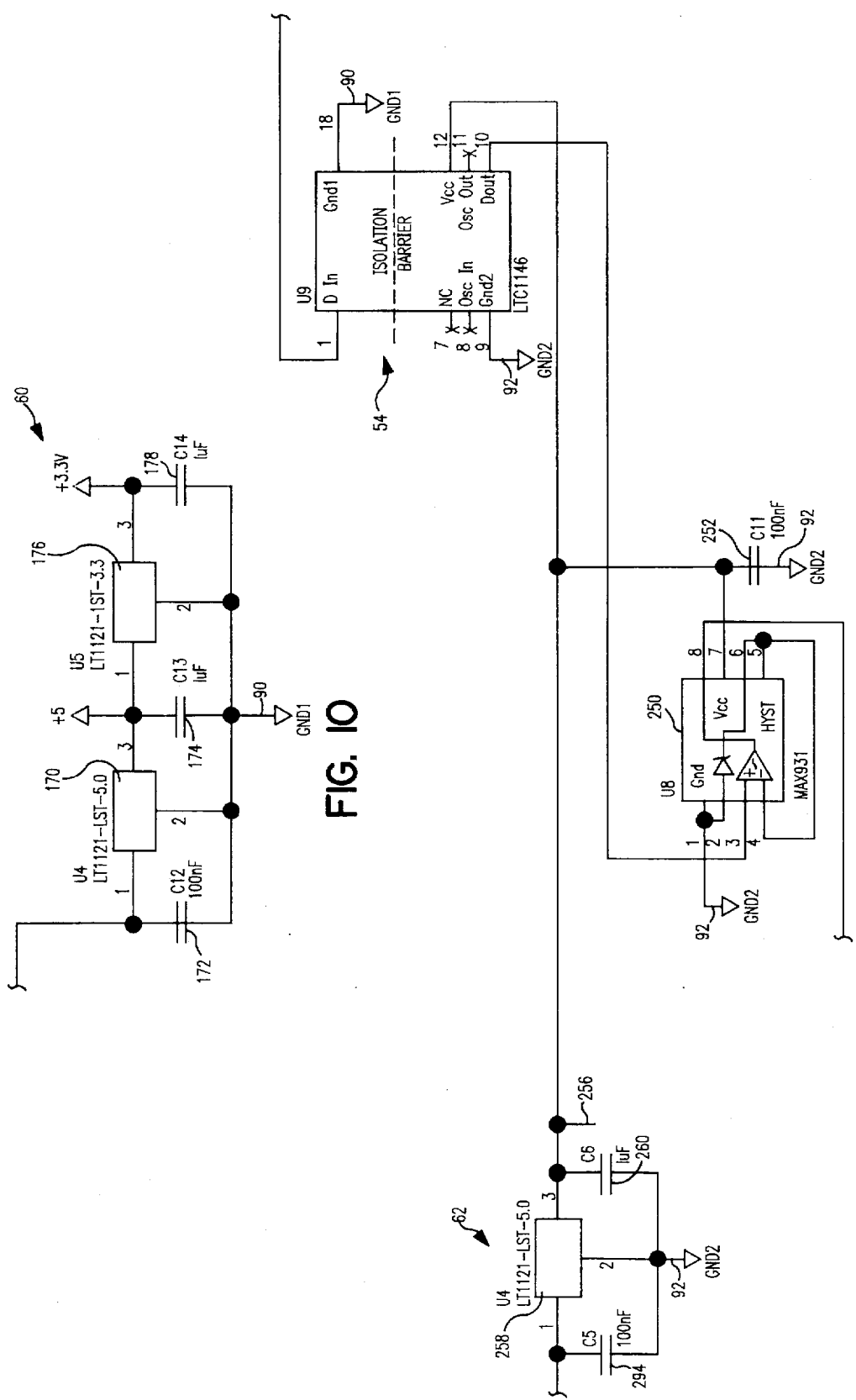

SENSOR AND TRANSMITTER WITH MULTIPLE OUTPUTS

BACKGROUND AND SUMMARY OF THE INVENTION

The present invention relates to a moisture sensor and transmitter, and particularly to a moisture sensor and transmitter with multiple outputs. More particularly, the present invention relates to an improved loop powered relative humidity and temperature sensing apparatus with multiple electrically isolated outputs.

Moisture measuring systems are well known for sensing moisture in a process pipe. Typical systems include remote transmitters with microprocessor electronics, a sensor element mounted in a probe, a flow chamber, a weather-proof enclosure and assorted fittings. The moisture probe can be installed onto a process pipe in a variety of ways. For instance, the moisture sensor can be mounted in an in-line mounting in a pipe, mounted in a pipe expansion, mounted in an elbow for small pipe diameters, or mounted in a by-pass line to facilitate removal of the moisture probe. See, for example, U.S. patent application Ser. No. 08/254,323 filed Jun. 6, 1994, which discloses such a moisture sensor and transmitter as well as a calibration therefor.

Conventional 4–20 mA loop powered transmitters are able to measure one or two process variables and can transmit one parameter by way of the loop. If it is desired to transmit more than one parameter using conventional 4–20 mA loop powered transmitters, additional individual 4–20 mA loop powered transmitters and additional power supplies are required. When controlling, for example, the climate in a room or a furnace, both the temperature and the relative humidity are parameters that are required to determine the quantity of moisture in the room. With conventional systems, the user typically provides both of these parameters to a programmable logic controller (PLC) or controller from individual loop powered transmitters so that the PLC or controller can calculate the desired quantified moisture units such as the absolute humidity or the mixing ratio.

What is needed is a single transmitter that can provide multiple outputs. Such transmitter could receive inputs from several sensors and provide several outputs without requiring additional powered transmitters. Users would particularly appreciate a measuring transmitter assembly that could manipulate the input signals from the sensors so that the output signals carried by the output loops indicate calculated quantified moisture units such as absolute humidity or mixing ratios. In addition, both manufacturers and users would appreciate a measuring transmitter assembly having multiple loops that are electrically isolated so that a single "common" ground connection could be used to ground all of the output loop circuits at the power supply allowing for the use of a single DC power supply to supply power to each of the loops.

According to the present invention, a measuring transmitter assembly is provided. The measuring transmitter assembly uses the same lines for power input and output signals. The measuring transmitter assembly includes a first sensor for providing a first input signal in response to the value of a first parameter. The measuring transmitter also includes a second sensor for providing a second input signal in response to the value of a second parameter. A transmitter is coupled to the first and second sensors. The transmitter includes a first output loop providing a first output signal in response to the first input signal and a second output loop providing a second output signal in response to the second input signal.

In preferred embodiments, the measuring transmitter in accordance with the present invention includes a first output loop providing a first output signal having a current that varies between 4 and 20 milliamps in response to a first input signal and a second output loop providing a second output signal having a current that varies between 4 and 20 milliamps in response to the second input signal. The first and second loops are electrically isolated by a digital isolator. The preferred digital isolator draws a current of 60 microamperes or less. The low power consumption of the digital isolator allows the measuring transmitter to include multiple isolated loops, each loop having a current that varies between 4 and 20 milliamps.

The low power consumption of the digital isolator allows the illustrative transmitter to utilize as many as all four pulse width modulation (PWM) outputs provided by the illustrative microcontroller so that the transmitter can include up to four output loop circuits. In this configuration, the transmitter could, for example, receive input signals from each of a first sensor, a second sensor, a third sensor, and a fourth sensor. The low power consumption of the digital isolator allows each of the first, second, third, and fourth output loop circuits to be electrically isolated.

In addition, each of the output loop circuits includes an independent ground portion that is maintained at a ground potential. Electrically isolating each of the output loop circuits allows for connecting the ground portions of each output loop at the power source to a single "common" ground connection. If the output loop circuits were not electrically isolated, the use of a common ground could result in interference between the output signals, potentially causing a malfunction of the transmitter. However, electrically isolating each of the output loop circuits allows for the use of a common ground at the power source without any of the output signals being affected by any of the other output signals.

Thus, the measuring transmitter assembly in accordance with the present invention can have process measurement signals that are provided to a single central microcontroller. The microcontroller calculates selected output parameters selected on the basis of a "unit's input signal" provided to the microcontroller in response to the position of a unit switch. The microcontroller, therefore, performs various mathematical functions on the input signals to determine the values of calculated parameters in order to provide "calculated output signals" that vary in response to the values of the calculated parameters and that are readily usable by a user without having to be processed through an external PLC or an external controller. These output signals are transmitted to the user by way of 4–20 mA output loop circuits.

The 4–20 mA output loop circuits are electrically isolated. Electrically isolating the output circuits allows the user to "common" the grounds of the output loops at the power supply without causing any interference between or in some other way affecting any of the output signals. This also allows the user to operate the measuring transmitter assembly with only one power supply providing power for all of the loops rather than providing a separate power supply for each loop. In addition, the low current consumption of the isolation barrier of the measuring transmitter assembly in accordance with the present invention allows for the use of multiple isolated 4–20 mA loop output circuits providing multiple 4–20 mA output signals.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 10 is a schematic diagram of a voltage regulator that provides electrical power to the first loop and that provides electrical power to various portions of the transmitter circuit; and FIG. 11 is a schematic diagram of a second voltage regulator that provides electrical power to the second loop, a comparator, and a digital isolator that isolates the first loop from the second loop.

DETAILED DESCRIPTION OF THE DRAWINGS

Figure 1:
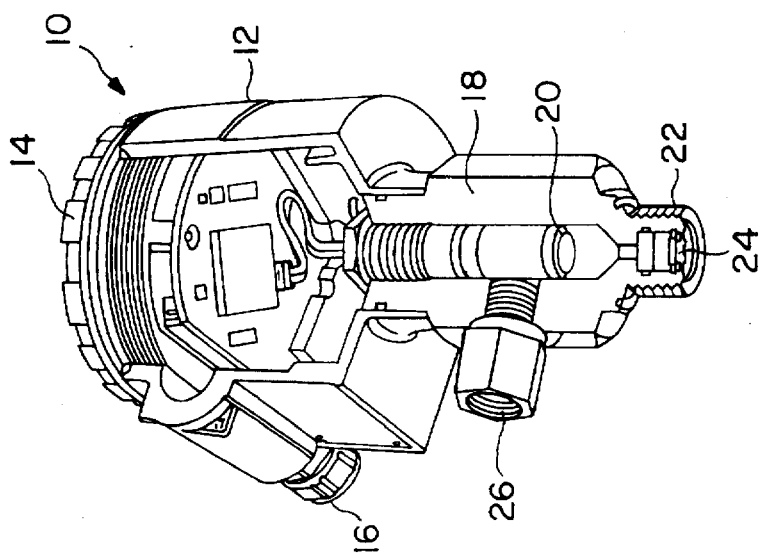
FIG. 1 is a perspective view with portions broken away illustrating details of a transmitter in accordance with the present invention for generating multiple output signals, such output signals optionally being proportional to measured parameters such as relative humidity and temperature detected by sensors and calculated parameters such as the dew point, the mixing ratio, and the absolute humidity that can be derived from the measured parameters.

Referring now to the drawings, FIG. 1 illustrates a transmitter 10 having an outer housing 12, a threaded cap portion 14, and a power signal cable entry 16. Illustratively, transmitter 10 is a DewPro MMR30 relative humidity moisture transmitter available from Endress+Hauser located in Greenwood, Ind. Transmitter 10 includes a flow cell 18 coupled to housing 12. Two sensor elements 20 are mounted within flow cell 18. Transmitter 10 also includes a threaded inlet or process connection 22 having a sintered filter 24 mounted therein. Transmitter 10 also includes an outlet or exhaust fitting 26 threadably coupled to flow cell 18. During normal operation, a plug having an orifice therein to bleed off process air is machined into the outlet fitting 26. Illustratively, transmitter 10 provides two two-wire output signals represented by two 4–20 mA loop currents which are directly proportional to measured or derived parameters such as the temperature and the relative humidity or the dew point.

Preferably, sensor elements 20 are relative humidity or trace moisture sensor elements operating under the capacitance principle. Sensor elements 20 are preferably mounted on an aluminum oxide ceramic substrate and have a reduced temperature coefficient. Typically, transmitter 10 is calibrated at the factory to precise National Institute of Standards and Technology (NIST) certified moisture references and has an accuracy of within ±2% relative humidity (RH) or ±2° C. dew point respectively.

Figure 2:
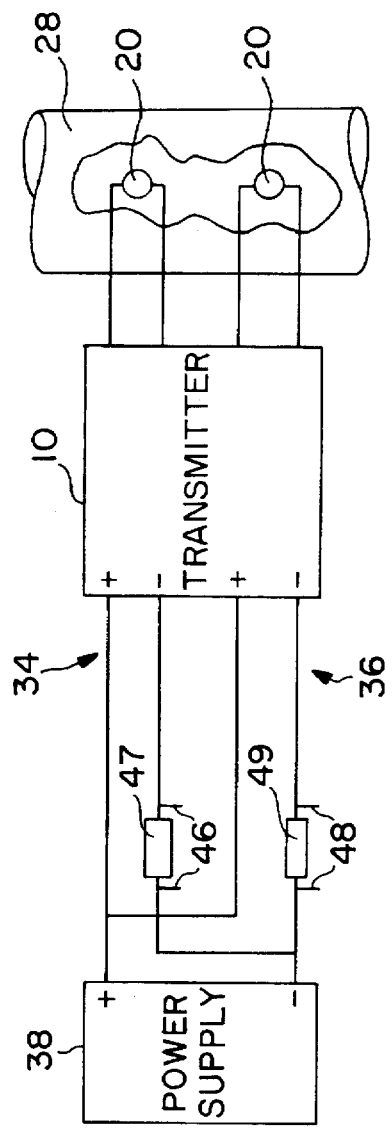
FIG. 2 is a block diagram illustrating the transmitter of FIG. 1 coupled to a process pipe, showing two sensors detecting parameters related to the contents of the pipe, the sensors providing signals to the transmitter, a power supply for providing power to the transmitter, and transmission loops connecting the power supply to the transmitter and carrying the transmitted signals from the transmitter to measuring resistors on the transmission loops for measuring the signals transmitted by the transmitter.

Transmitter 10 can accept input signals from a plurality of sensor elements 20 as shown diagrammatically in FIG. 2. Illustratively, transmitter 10 is mounted so that sensor elements 20 detect parameters related to the contents of process pipe 28. Transmitter 10 is illustratively connected to two isolated transmission loops 34, 36, each loop 34, 36 transmitting an output signal proportional either to the measured parameters or to parameters derived from the measured parameters. The output signal associated with loop 34 is measured at terminals 46 adjacent to a first measuring resistor 47 and the output signal associated with loop 36 is measured at terminals 48 adjacent to a second measuring resistor 49.

Transmission loops 34, 36 also operate to supply electrical power to transmitter 10. Isolating loops 34, 36, inside of transmitter 10 rather than at power supply 38 allows for powering both loops 34, 36 from the same power supply and for connecting the ground portion of each loop 34, 36 to a single "common" ground connection at the power supply.

Figure 3:
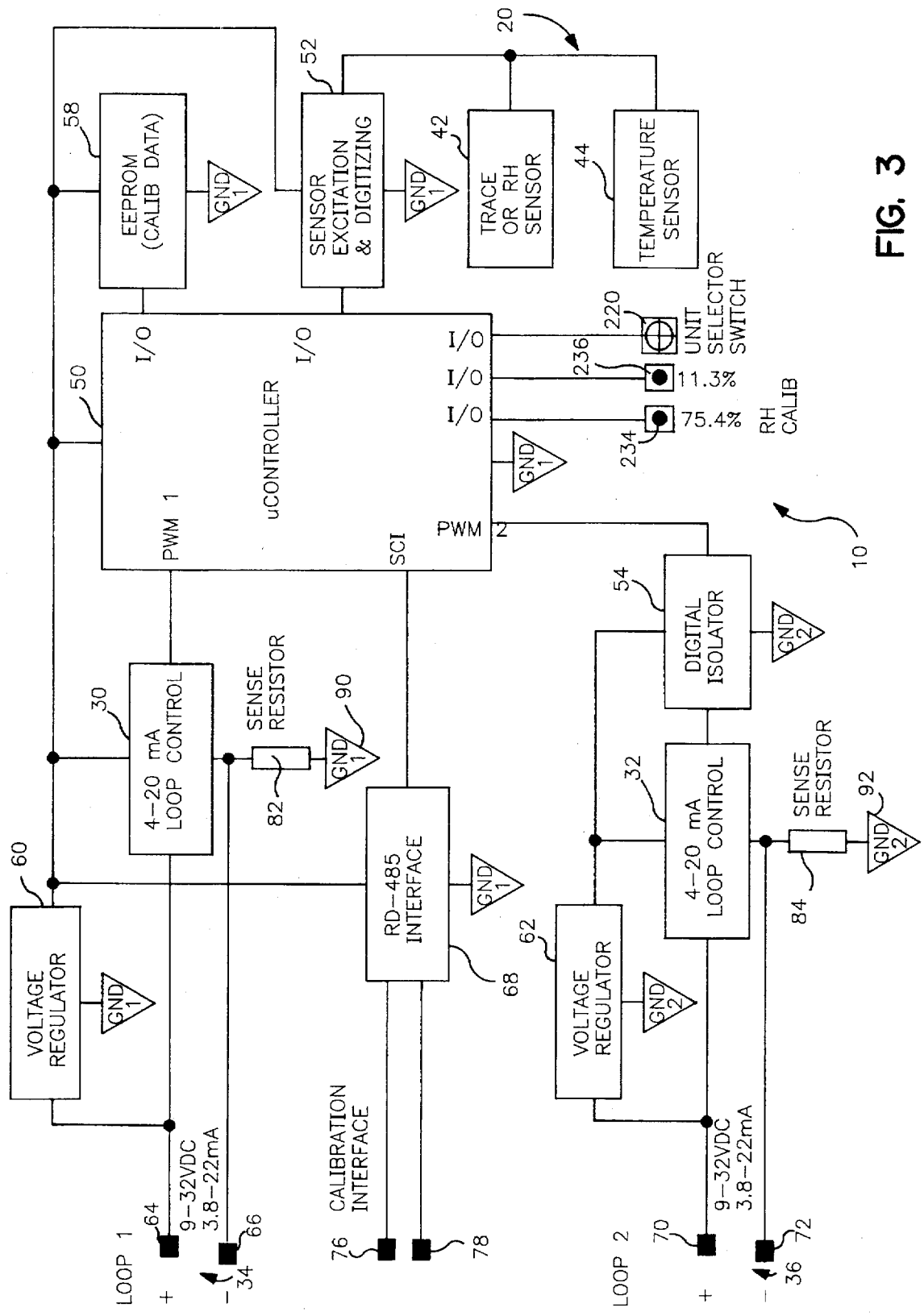
FIG. 3 is a block diagram illustrating the electronic circuitry of the transmitter and showing illustrative temperature and trace or relative humidity sensors, a microcontroller that receives conditioned signals originating from the sensors, an EEPROM that stores and provides data to the microcontroller, and a switch that provides an input to the microcontroller in response to the configuration of the switch, a first transmission loop coupled to the microcontroller for transmitting an output signal from the microcontroller to the receiver (not shown), and a second transmission loop coupled to the microcontroller for transmitting a second output signal from the microcontroller to the receiver.

FIG. 3 is a block diagram of the electronics of an illustrative transmitter 10 that provides two two-wire output signals in response to input signals from sensors 20, illustratively including an RH sensor 42 and a temperature sensor 44. A microcontroller 50 is provided for controlling the electronics to process information from sensors 42, 44, an EEPROM 58, and an RS-485 communication interface 68 and to provide signals to loops 34, 36.

An RS-485 communication interface 68 is coupled to microcontroller 50. Interface 68 is configured to be coupled to transmitter 10 by terminals 76, 78 of a calibration interface to permit a calibrator (not shown) to calibrate transmitter 10. During calibration of transmitter 10, data is transmitted from the calibrator to EEPROM 58 through microcontroller 50.

Calibration data is stored in EEPROM 58 as shown 35 in FIG. 3. EEPROM 58 is electrically coupled to I/O pins of microcontroller 50. A first voltage regulator 60 is provided to supply power to the various electronic components of transmitter 10 including a first loop control circuit 30. A second voltage regulator 62 is provided to supply power to various other electronic components of transmitter 10 including a second loop control circuit 32.

First loop control circuit 30 is provided to generate a first output signal ranging from 4–20 mA indicative of the parameters of interest measured by a first sensor 20 or mathematically derived from parameters measured by both sensors 20. Second loop control circuit 32 is provided to generate a second output signal ranging from 4–20 mA indicative of the parameters of interest measured by another of sensors 20. Illustratively, the output from loop control 30 across terminals 64, 66 is a dew point temperature in °C. or °F. If desired, transmitter 10 in accordance with the present invention can be configured to include a third loop control circuit (not shown) to generate a third output signal ranging from 4–20 mA indicative of a parameter of interest and a fourth loop control circuit (not shown) to generate a fourth output signal ranging from 4–20 mA indicative of a parameter of interest.

Transmitter 10 includes a digital isolator 54 to electrically isolate 4–20 mA circuits 30, 32 as shown in FIG. 3. Digital isolator 54 is illustratively a model number LTC1146 available from Linear Technology. Digital isolator 54 isolates the digital signal from microcontroller 50 and then outputs the signal to the loop control 32.

Typically, electrical circuits are isolated using optoisolators or DC/DC converters using transformers. However, these devices typically consume too much current to be practical for use with a 4–20 mA loop powered device. Digital isolator 54, however, isolates circuits 30, 32 while typically consuming only 60 micro amperes. This low power consumption allows transmitter 10 to include up to four 4–20 mA loop control circuits 30, 32.

Figure 4:
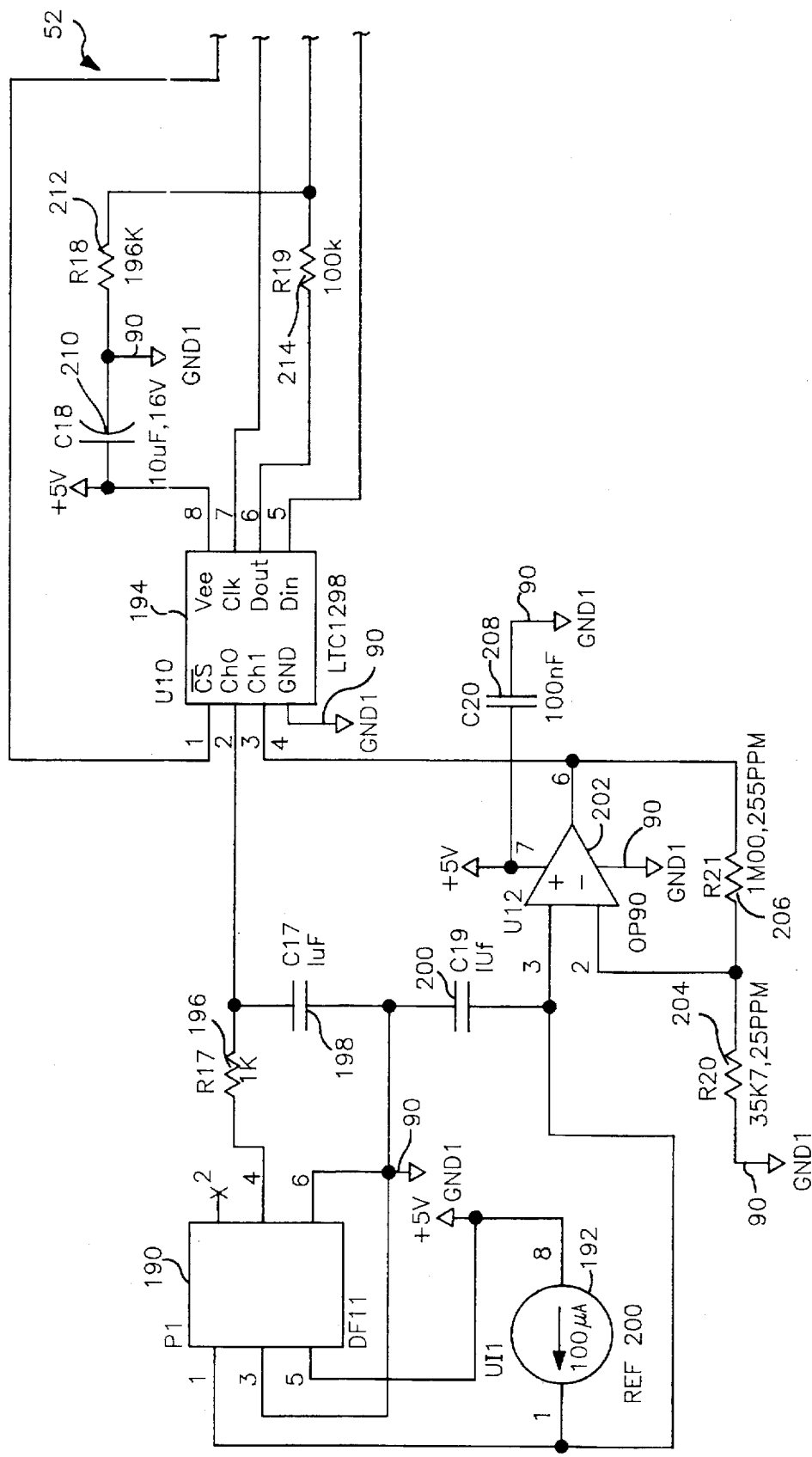
FIG. 4 is a schematic diagram of the sensor conditioning and digitizing circuitry that illustratively receives two analog signals from the sensors and provides a digital signal in response to each analog signal received.
Figure 6:
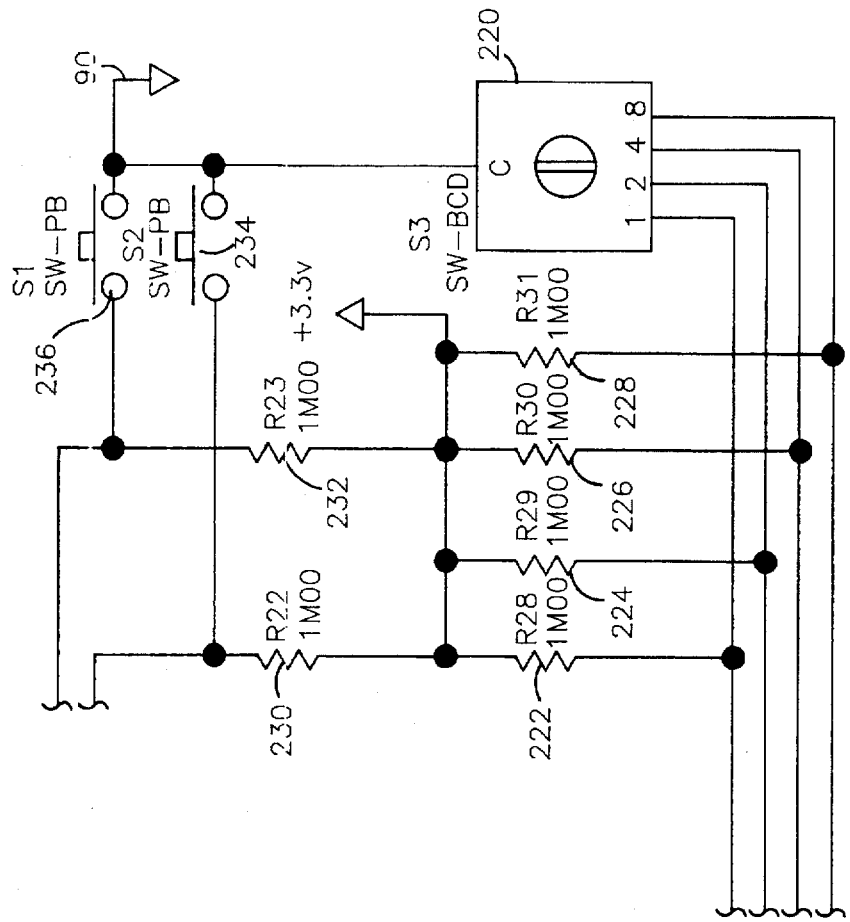
FIG. 6 is a schematic diagram of a binary coded decimal (BCD) selector switch and calibration switches that provide calibration and unit selection inputs to the microcontroller.
Figure 5:
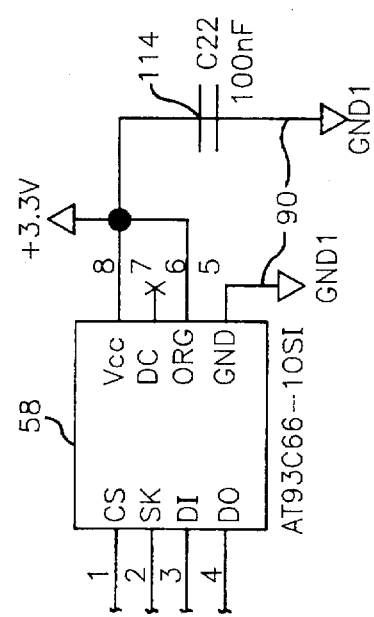
FIG. 5 is a schematic diagram of the EEPROM that stores calibration data and calculation data used during the calculation of derived values from the measured parameters, the calculation and calibration data being stored for use by the microcontroller.
Figure 7:
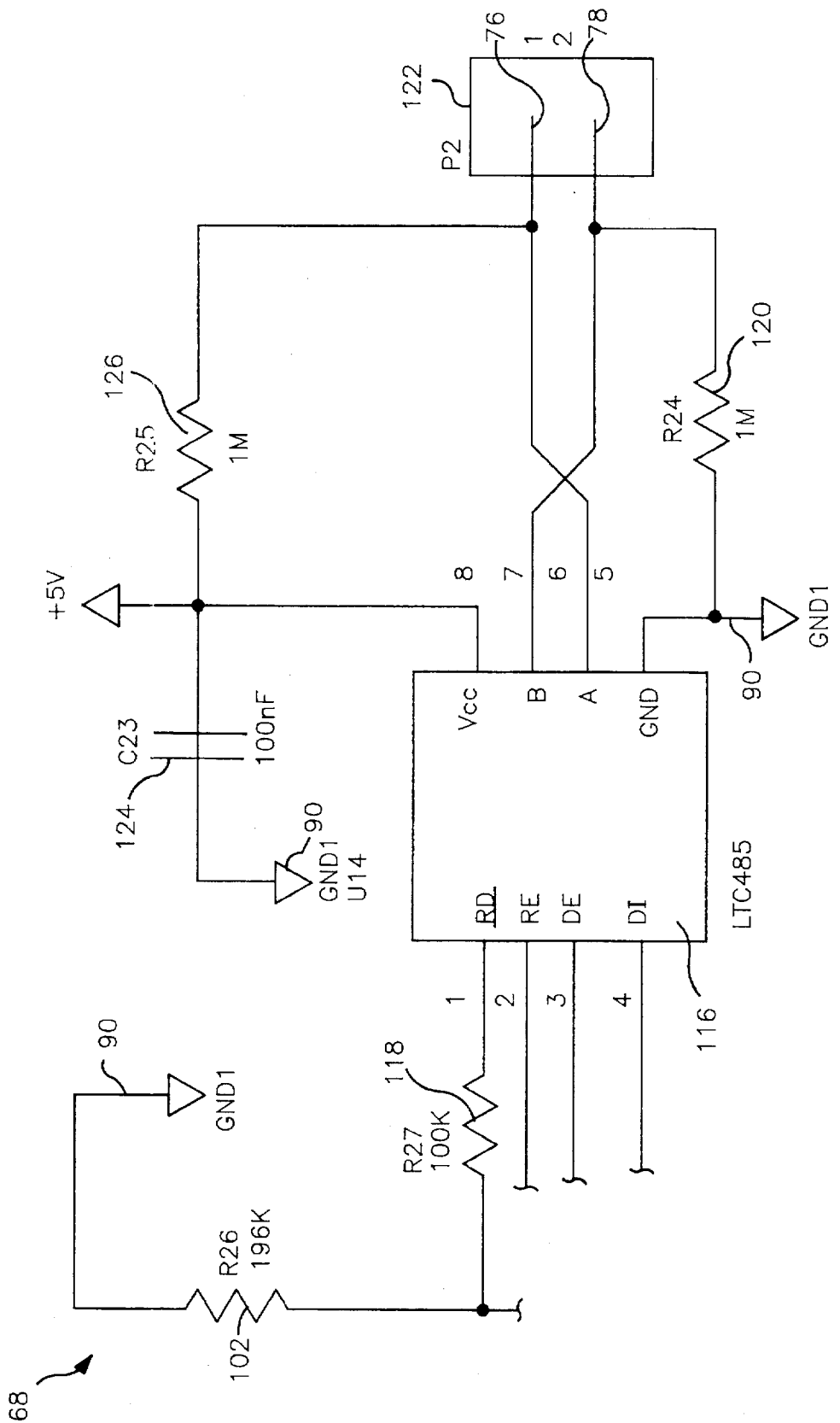
FIG. 7 is a schematic diagram of an RS-485 interface that allows for the uploading and downloading of calibration data between the transmitter and a data transfer unit (not shown) as well as for diagnostic evaluation of the transmitter.
Figure 8:
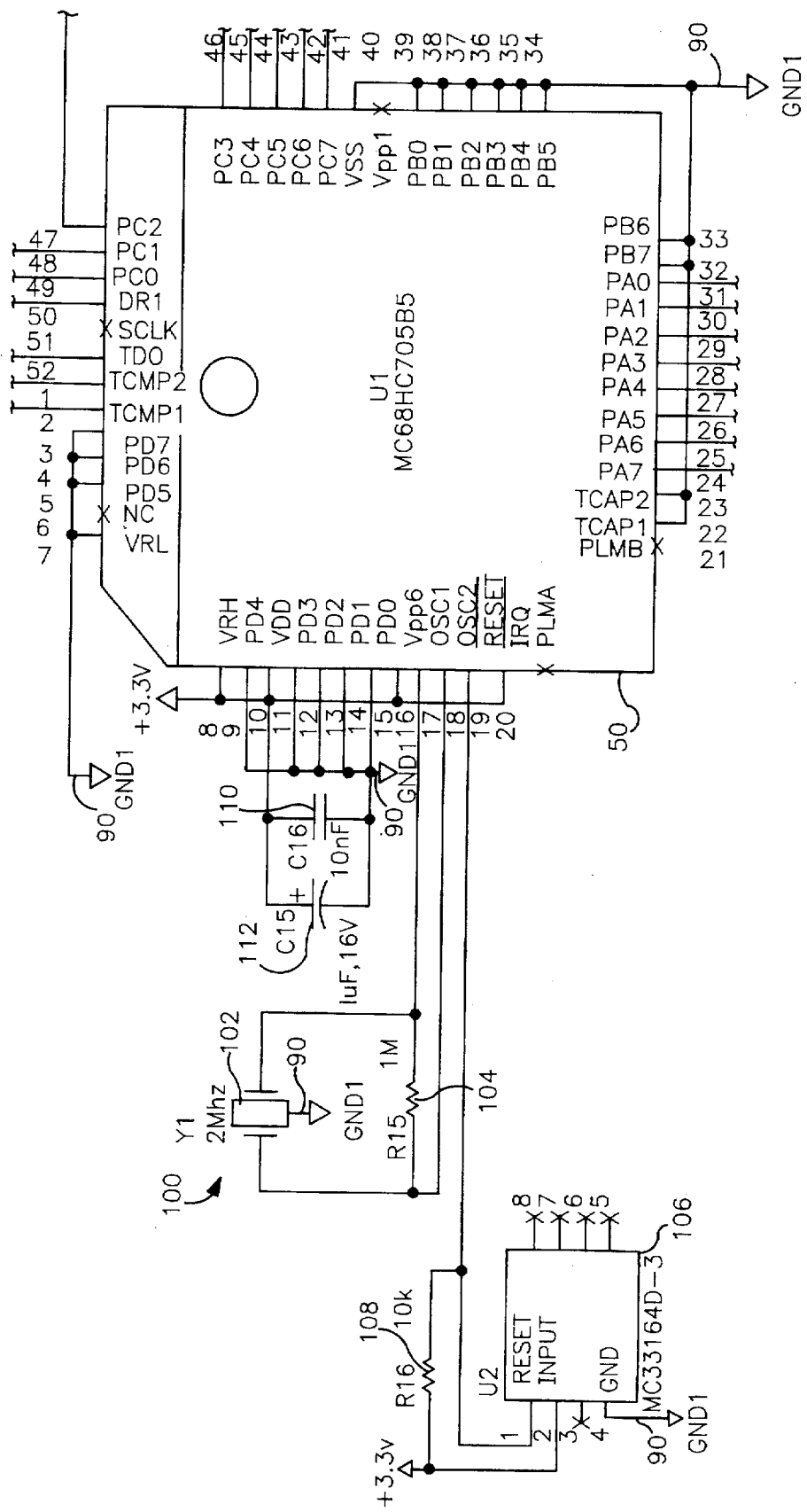
FIG. 8 is a schematic diagram of a microcontroller that links the RS-485 interface with the EEPROM and that provides output signals proportional to the measured and derived parameters in response to inputs from the sensors, the switches, and the EEPROM.

Details of the electronic circuitry of transmitter 10 are illustrated in FIGS. 4–11. Microcontroller 50 is illustratively a model number MC68HC705B5 available from Motorola as shown in FIG. 8. Microcontroller 50 receives inputs from sensor excitation and digitizing circuit 52 as shown in FIG. 4, EEPROM 58 as shown in FIG. 5, a unit selector switch 220, and RH calibration switches 234, 236 as shown in FIG. 6, and RS-485 interface 68 shown in FIG. 7. Unit selector switch 220 is positionable by the user at discrete positions to indicate the desired units of the output signals. Illustratively, unit selector switch 220 is a #NDR3FR10P binary coded decimal (BCD) selector switch available from NKK. RH calibration switches 234, 236 are adjustable to cause an adjustment of the output signals and are useful for calibrating transmitter 10. Illustratively, RH calibration switches 234, 236 are #7914J-1-000 switches available from Bourns.

Sensor conditioning and digitizing circuit 52 shown in FIG. 4 includes connector 190 which is coupled to sensors (not shown in FIG. 4), for example, a Relative Humidity (RH) sensor and a temperature sensor. Pin 1 of connector 190 is coupled to pin 1 of a 100 uA constant current source 192. Illustratively, 100 uA constant current source 192 is a Model No. REF200 AU constant current source available from Burr Brown. Pin 3 of connector 190 is coupled to an internal first ground 90 of transmitter 10. Pin 5 of connector 190 is coupled to the +5V supply voltage. Pin 5 of connector 190 is also coupled to pin 8 of 100 uA constant current source 192. Pin 4 of connector 190 is coupled to a 1K resistor 196. 1K resistor 196 is coupled to pin 2 of 10 bit analog to digital converter (A/D converter) 194. Illustratively, A/D converter 194 is a Model No. LTC1298ISA 10 bit analog to digital converter available from Linear Technology. The common terminal of resistor 196 and pin 2 of A/D converter 194 is coupled to pin 6 of connector 190 through 1 uF capacitor 198. The common terminal of pin 6 of connector 190 and 1 uF capacitor 198 is coupled to first ground 90. In addition, the common terminal of pin 6 of connector 190 and of 1 uF capacitor 198 is coupled to the +input terminal of operational amplifier 202 at pin 3 through 1 uF capacitor 200. The common terminal of pin 1 of connector 190 and pin 1 of 100 uA constant current source 192 is connected to the common terminal of the +input terminal of operational amplifier 202 at pin 3 and the 1 uF capacitor 200.

Illustratively, operational amplifier 202 is a model number OP-90GS available from Analog Devices. The −input terminal of operational amplifier 202 at pin 2 is coupled to first ground 90 through 35K resistor 204. The common terminal of pin 2 of operational amplifier 202 and 35K resistor 204 is coupled to pin 6 of operational amplifier 202 through 1M resistor 206. Pin 4 of operational amplifier 202 is coupled to first ground 90. Pin 7 of operational amplifier 202 is coupled to a +5V supply voltage. In addition, the common terminal of pin 7 of operational amplifier 202 and the +5V supply voltage is coupled to first ground 90 through 100 nF capacitor 208.

The common terminal of pin 6 of operational amplifier 202 and 1M resistor 206 is coupled to pin 3 of A/D converter 194 as shown in FIG. 4. Pin 4 of A/D converter 194 is coupled to first ground 90. Pin 8 of A/D converter 194 is coupled to a +5V power supply. In addition, the common terminal of pin 8 of A/D converter 194 and the +5V power supply is coupled to first ground 90 through 10 uF capacitor 210. Pin 6 of A/D converter 194 is coupled to first ground 90 through 100K resistor 214 and 196K resistor 212. The common terminal of 100K resistor 214 and 196K resistor 212 is coupled to pin 26 of microcontroller 50. Pin 1 of A/D converter 194 is coupled to pin 24 of microcontroller 50. Pin 7 of A/D converter 194 is coupled to pin 27 of microcontroller 50. Pin 5 of A/D converter 194 is coupled to pin 25 of microcontroller 50.

The preferred RH sensor (not shown) provides a voltage to connector 190 that is proportional to the RH. This signal is fed into a low pass filter comprising 1K resistor 196 and 1 uF capacitor 198, and then to one of two inputs of A/D converter 194. The A/D converter 194 digitizes the voltage and provides an output signal of the digital value of the voltage to microcontroller 50 via a 4-wire serial communication link as described above.

The preferred temperature sensor (not shown) has a variable resistance that varies proportionally with the sensed temperature. The 100 uA constant current source 192 and the variable resistance of the temperature sensor cooperate to provide a voltage that varies with the sensed temperature. This voltage signal is amplified via operational amplifier 202, 35K resistor 204, and 1M resistor 206. The output of operational amplifier 202 is received by the A/D converter 194. The A/D converter 194 digitizes the signal and provides the digital value to microcontroller 50 via the 4-wire serial communication link.

Microcontroller 50 collects the digitized input signals from sensor excitation and digitizing circuit 52 and calculates the actual RH and temperature using these digitized input signals and calibration data stored in EEPROM 58.

From RH and temperature, microcontroller 50 then calculates the desired moisture unit, for example, dew point, mixing ratio, or absolute humidity, based on the position of the BCD selector switch 220 as shown in FIG. 6.

Pin 1 of selector switch 220 shown in FIG. 6 is coupled to pin 31 of microcontroller 50. Pin 2 of selector switch 220 is coupled to pin 30 of microcontroller 50. Pin 4 of selector switch 220 is coupled to pin 29 of microcontroller 50. Pin 8 of selector switch 220 is coupled to pin 28 of microcontroller 50. In addition, pin 1 of selector switch 220 is coupled to 1M resistor 222. Pin 2 of selector switch 220 is coupled to 1M resistor 224. Pin 4 of selector switch 220 is coupled to 1M resistor 226. Pin 8 of selector switch 220 is coupled to 1M resistor 228. Resistors 222, 224, 226, 228 are coupled in parallel to a +3.3V power supply. In addition, a common terminal of resistors 222, 224, 226, 228 is coupled to pin 42 of microcontroller 50 through a 1M resistor 230. Also, the common terminal of resistors 222, 224, 226, 228 is coupled to pin 43 of microcontroller 50 through 1M resistor 232.

Pin C of selector switch 220 is coupled to first ground 90 as shown in FIG. 6. Pin C of selector switch 220 is also coupled to push button switches 234, 236 that are used for field recalibration of the RH sensor. The common terminal of pin 42 of microcontroller 50 and 1M resistor 230 is coupled to first ground 90 through push button switch 234. The common terminal of pin 43 of microcontroller 50 and 1M resistor 232 is coupled to first ground 90 through push button switch 236.

A 2 MHz clock 100 includes a 2 MHz oscillator 102 coupled in parallel with a 1M resistor 104 between pins 16 and 17 (OSC1 and OSC2) of microcontroller 50 as shown in FIG. 8. Pin 1 of low voltage interrupt chip 106 is coupled to pin 18 of microcontroller 50. Pin 1 of chip 106 is also coupled through a 10K resistor 108 to pin 2 of chip 106. The common terminal of resistor 108 and pin 2 of chip 106 is coupled to the +3.3V supply voltage. Pin 4 of chip 106 is coupled to first ground 90. Chip 106 measures the supply voltage and resets the microcontroller 50 if the voltage drops below a preset value.

Pins 3, 4, 5, 7, 9, 11–14, 22, 23, 32, 33, 34–39, and 41 of microcontroller 50 are all coupled to first ground 90 as shown in FIG. 8. Pins 8, 10, 15, and 19 of microcontroller 50 are coupled to the +3.3V supply voltage. Pin 10 of microcontroller 50 is coupled through a 100 nF capacitor 110 and 1 uF capacitor 112 which is in parallel to 100 nF capacitor 110 to first ground 90.

Pin 44 of microcontroller 50 is coupled to pin 4 of EEPROM chip 58 as shown in FIG. 5. Illustratively, chip 58 is a AT93C66-10SI EEPROM chip available from Atmel. Pin 45 of microcontroller 50 is coupled to pin 3 of chip 58. Pin 46 of microcontroller 50 is coupled to pin 2 of chip 58. Pin 47 of microcontroller 50 is coupled to pin 1 of chip 58.

Pin 5 of chip 58 is coupled to first ground 90 as shown in FIG. 5. Pin 6 of chip 58 is coupled to pin 8 of chip 58. The common terminal of pin 6 and pin 8 is coupled to the +3.3V supply voltage. In addition, the common terminal of pins 6 and 8 are coupled through a 100 nF capacitor 114 to first ground 90.

Pin 48 of microcontroller 50 is coupled to pin 3 of communication interface chip 116 of RS-485 interface as shown in FIG. 7. Illustratively, chip 116 is a LTC485 chip available from Linear Tech. Pin 49 of microcontroller 50 is coupled to pin 2 of chip 116. Pin 50 of microcontroller 50 is coupled through a 100K resistor 118 to pin 1 of chip 116. In addition, the common terminal of 100K resistor 118 and pin 50 of microcontroller 50 is coupled through a 196K resistor 102 to first ground 90. Pin 52 of microcontroller 50 is coupled to pin 4 of chip 116. Pin 5 of chip 116 is coupled to first ground 90. Pin 5 of chip 116 is also coupled through a 1M resistor 120 to pin 2 of connector 122. Pin 6 of chip 116 is coupled to pin 1 of connector 122. Pin 7 of chip 116 is coupled to pin 2 of connector 122. Pin 8 of chip 116 is coupled to a +5V supply voltage. The common terminal of the +5V supply voltage and pin 8 of chip 116 is also coupled through a 100 nF capacitor 124 to first ground 90. In addition, the common terminal of the +5V supply voltage and pin 8 of chip 116 is coupled through a 1M resistor 126 to pin 1 of connector 122.

Figure 9:
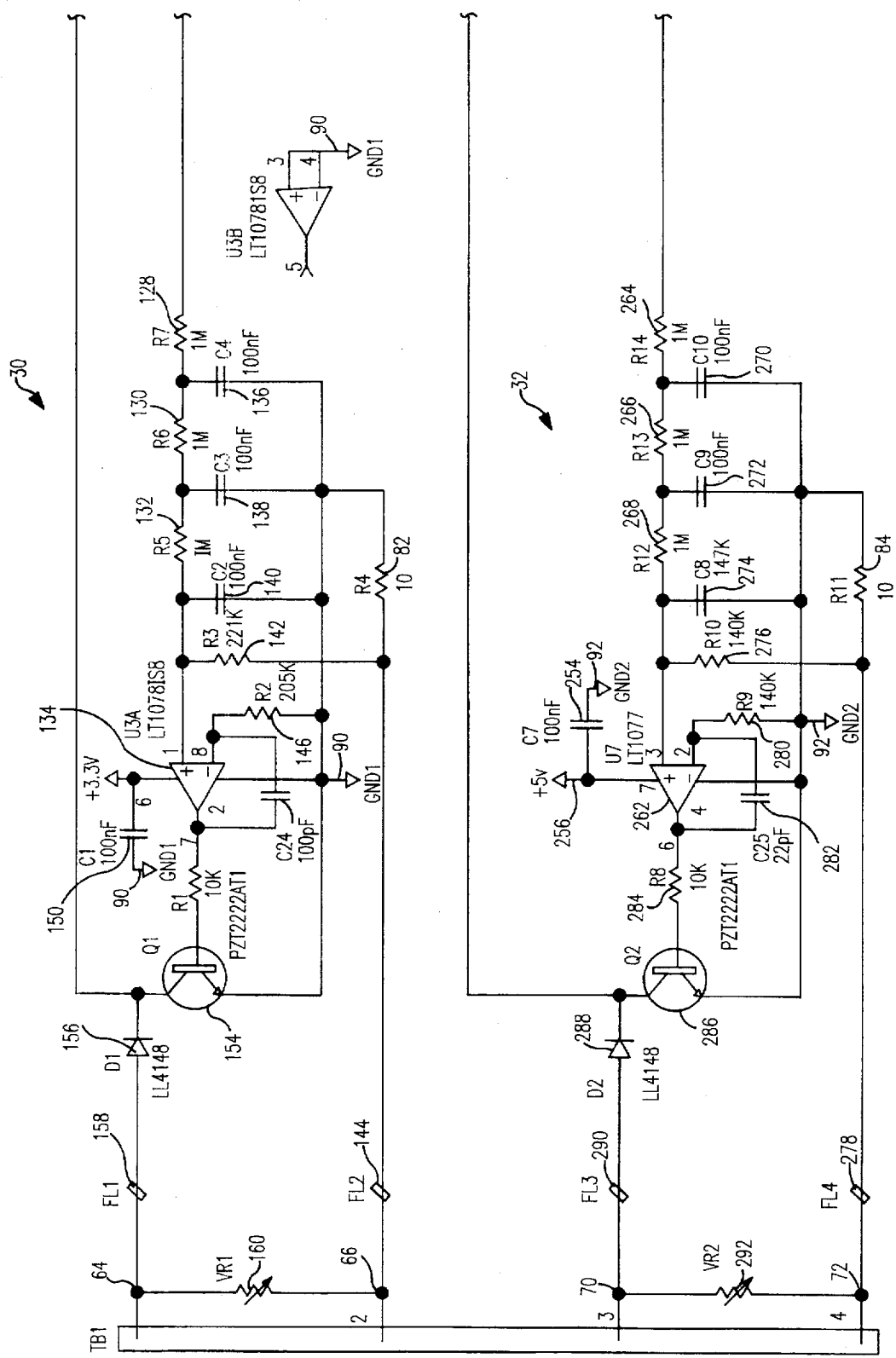
FIG. 9 is a schematic diagram of two separate and electrically isolated transmission loops, each loop transmitting an output signal proportional to the value of a measured or derived parameter.

Pin 2 of microcontroller 50 is coupled to first loop control circuit 30 as shown in FIG. 9. Specifically, pin 2 of microcontroller 50 is coupled through a 1M resistor 128, a 1M resistor 130, and a 1M resistor 132 to the +input terminal at pin 1 of operational amplifier 134. Operational amplifier 134 is a model number LT1078IS8 available from Linear Tech. The common terminal of resistors 128 and 130 is coupled to first ground 90 through a 100 nF capacitor 136. The common terminal of resistors 130 and 132 is coupled to first ground 90 through a 100 nF capacitor 138. The common terminal of resistor 132 and the +input terminal at pin 1 of operational amplifier 134 is coupled through a 100 nF capacitor 140 to first ground 90. The common terminal of resistor 132 and the +input terminal at pin 1 of operational amplifier 134 is also coupled through a 221 mK resistor 142 and 10 ohm sense resistor 82 to first ground 90. A common terminal of resistors 142 and 82 is coupled through a ferrite bead 144 to output terminal 66. The −input terminal of operational amplifier 134 at pin 8 is coupled through a 205K resistor 146 to first ground 90. Pin 8 of operational amplifier 134 is also coupled through a 100 pF capacitor 148 to the output terminal of operation amplifier 134 at pin 7. Pin 2 of operational amplifier 134 is coupled to first ground 90. Pin 6 of operational amplifier 134 is coupled to the +3.3V supply voltage. In addition, pin 6 of operational amplifier 134 is coupled through a 100 nF capacitor 150 to first ground 90. The common terminal of capacitor 148 and the output terminal at pin 7 of operational amplifier 134 is coupled through a 10K resistor 152 to the base of transistor 154. Illustratively transistor 154 is a MJD31 transistor available from Motorola. The emitter of transistor 154 is coupled to first ground 90. The collector of transistor 154 is coupled to the cathode of diode 156. Diode 156 is illustratively a LL4148 diode available from ITT. The anode of diode 156 is coupled through ferrite bead 158 to terminal 64. An overvoltage suppressor 160 is coupled to terminal 64 and to terminal 66.

The common terminal of the cathode of diode 156 and the collector of transistor 154 is also coupled to pin 1 of voltage regulator 170 as shown in FIG. 10. Illustratively, voltage regulator 170 is a LT1121-IST-5.0 regulator available from Linear Tech. The common terminal of the cathode of diode 156, the collector of transistor 154, and pin 1 of regulator 170 is coupled through a 100 nF capacitor 172 to first ground 90. Pin 2 of regulator 170 is coupled to first ground 90. Pin 3 of regulator 170 is coupled to a +5V supply voltage. Pin 3 of regulator 170 is also coupled through a 1 uF capacitor 174 to first ground 90. In addition, the common terminal of the +5V supply voltage, capacitor 174, and pin 3 of regulator 170 is coupled to pin 1 of voltage regulator 176. Illustratively, voltage regulator 176 is a LT1121-IST-3.3 regulator available from Linear Tech. Pin 2 of regulator 176 is coupled to first ground 90. Pin 3 of regulator 176 is coupled to the +3.3V supply voltage. Pin 3 of regulator 176 is also coupled through a 1 uF capacitor 178 to first ground 90.

Pin 1 of microcontroller 50 is coupled to pin 1 of digital isolator 54 as shown in FIG. 11. Illustratively, digital isolator 54 is a LTC1146CN digital isolator available from Linear Technologies. Pin 18 of digital isolator 54 is coupled to first ground 90. Pin 9 of digital isolator 54 is coupled to an internal second ground 92 of transmitter 10. Pin 10 of digital isolator 54 is coupled to pin 3 of a comparator 250. Pin 12 of digital isolator 54 is coupled to voltage regulator 62 as well as to pin 7 of comparator 250.

Specifically, pin 12 of digital isolator 54 is coupled to second ground 92 through a 100 nF capacitor 252 as shown in FIG. 11. The common terminal of pin 12 of digital isolator 54 and 100 nF capacitor 252 is coupled by a common terminal 256 shown in FIG. 11 to second ground 92 through 100 nF capacitor 254 as shown in FIG. 9. The common terminal 256 of pin 12 of digital isolator 54, 100 nF capacitor 252, and 100 nF capacitor 254 is also coupled to pin 3 of voltage regulator 258 as shown in FIG. 11. The common terminal of pin 3 of voltage regulator 258 and terminal 256 is coupled to second ground 92 through 1 uF capacitor 260. In addition, the common terminal of pin 3 of voltage regulator 258 and terminal 256 is coupled to pin 7 of operational amplifier 262 as shown in FIG. 9. In addition, pin 7 of operational amplifier 262 is coupled to second ground 92 through 100 nF capacitor 254. Illustrative operational amplifier 262 is a Model No. LT1077S8 operational amplifier available from Linear Technologies.

The common terminal of pin 12 of digital isolator 54 and 100 nF capacitor 252 is coupled to pin 7 of comparator 250 as shown in FIG. 11. Illustrative comparator 250 is a Model No. MAX931ESA comparator available from Maxim. Pins 1 and 2 of comparator 250 are coupled to second ground 92. Pin 3 of comparator 250 is coupled to pin 10 of digital isolator 54. Pin 4 of comparator 250 is coupled to pin 5 of comparator 250. Pin 6 of comparator 250 is coupled to the common terminal of pin 4 of comparator 250 and pin 5 of comparator 250.

Pin 8 of comparator 250 is coupled through a 1M resistor 264, a 1M resistor 266, and a 1M resistor 268 to the +input terminal of operational amplifier 262 at pin 3 as shown in FIG. 9. The common terminal of resistors 264 and 266 is coupled to second ground 92 through a 100 nF capacitor 270. A common terminal of resistors 266 and 268 is coupled to second ground 92 through a 100 nF capacitor 272. The +input terminal at pin 3 of operational amplifier 262 is coupled through a 100 nF capacitor 274 to second ground 92. The common terminal of pin 3 of operational amplifier 262, resistor 268, and capacitor 274 is also coupled through a 147K resistor 276 and 10 ohm sense resistor 84 to second ground 92. A common terminal of resistors 276 and 84 is coupled through a ferrite bead 278 to output terminal 72. The –input terminal of operational amplifier 262 at pin 2 is coupled through a 140K resistor 280 to second ground 92. The common terminal of resistor 280 and pin 2 of operational amplifier 262 is also coupled through a 22 pF capacitor 282 to the output terminal of operation amplifier 262 at pin 6. Pin 4 of operational amplifier 262 is coupled to second ground 92. The output terminal at pin 6 of operational amplifier 262 is coupled through a 10K resistor 284 to the base of transistor 286. Illustratively transistor 286 is a MJD31 transistor available from Motorola. The emitter of transistor 286 is coupled to second ground 92. The collector of transistor 286 is coupled to the cathode of diode 288. Diode 288 is illustratively a LL4148 diode available from ITT. The anode of diode 288 is coupled through ferrite bead 290 to terminal 70. An overvoltage suppressor 292 is coupled to terminal 70 and to terminal 72.

The common terminal of the cathode of diode 288 and the collector of transistor 286 is also coupled to pin 1 of voltage regulator 258 as shown in FIG. 11. Illustratively, voltage regulator 258 is a LT1121-IST-5.0 regulator available from Linear Tech. Pin 1 of regulator 258 is coupled through a 100 nF capacitor 294 to second ground 92. Pin 2 of regulator 258 is coupled to second ground 92. Pin 3 of regulator 258 is coupled through a 1 uF capacitor 260 to second ground 92. In addition, the common terminal of pin 3 of regulator 258 and capacitor 260 is coupled to the common terminal 256 of pin 12 of digital isolator 54, 100 nF capacitor 252, 100 nF capacitor 254, and pin 7 of operational amplifier 262 as described above.

In preferred embodiments, microcontroller 50 collects input signals from RH sensor 42 and temperature sensor 44 and calculates the actual RH and temperature using calibration data stored in EEPROM 58 as shown in FIG. 3. Microcontroller 50 then calculates a desired moisture unit such as dew point, mixing ratio, or absolute humidity based on the setting of BCD selector switch 220. A signal corresponding to the selected moisture unit is then output to first 4–20 mA. loop controller 30 from pin 2 of microcontroller 50 in pulse width modulation (PWM) format. PWM format is a square wave in which the frequency is fixed, but the duty cycle varies proportionally with the unit of interest. The PWM values corresponding to 4 mA and 20 mA for the moisture units are calibration values that are stored in EEPROM 58.

Likewise, a signal corresponding to the temperature is output to second 4–20 mA loop controller 32 from pin 1 of microcontroller 50 in PWM format. The PWM values corresponding to 4 mA and 20 mA for temperature are also calibration values that are stored in EEPROM 58. Although only two loops 30, 32 are included in the presently preferred embodiment, other pins are available on microcontroller 50 to generate digital signals corresponding additional parameters for output to additional 4–20 mA loops.

The PWM signal from pin 2 of microcontroller 50 to first 4–20 mA loop controller 30 is converted from the square wave to an analog voltage via resistors 128, 130, 132, and capacitors 136, 138, 140. The analog voltage is then converted into a current by resistors 146, 142, 152, 82, operational amplifier 134, and transistor 154. Sense resistor 82 allows operational amplifier 134 to compensate for the current consumption of the circuit and therefore maintains an output current directly proportional to the input voltage.

The PWM signal from pin 1 of microcontroller 50 to second 4–20 mA loop controller 32 is electrically isolated by digital isolator 54 and then output to comparator 250. Comparator 250 maintains a consistent high level and low level amplitude of the PWM signal. The amplitude of the output from digital isolator 54 varies as changes in the ambient temperature cause the temperature of digital isolator 54 to vary. The output from comparator 250 is much less temperature dependent and use of comparator 250 virtually eliminates this potential drift error.

The process measurement signals from sensors 20 are provided to a single microcontroller 50, allowing for the calculation of various output values based on the input signals. This allows transmitter 10 to calculate various parameters based on the input signals and to provide the calculated values rather than providing just the raw measured values, so that users no longer need to manipulate the output signals to obtain the desired parameter values. Of course if desired, illustrative transmitter 10 can provide the raw measured values.

In addition, use of digital isolator 54 to isolate loop control circuits 30, 32 minimizes the amount of power consumed by the isolation barrier as compared to other isolation devices such as transformers and opto-isolators. Lowering the power consumption of the isolation barrier allows for the use of multiple loop control circuits and multiple loops carrying 4–20 mA signals. Illustrative transmitter 10 can include up to four 4–20 mA loop control circuits and output loops when additional digital isolators similar to digital isolator 54 are used to isolate the loop control circuits.

The power consumption of digital isolator 54 does not limit transmitter 10 to four 4–20 mA output loops. Transmitter 10 is limited to four 4–20 mA output loops by the number of PWM outputs available on illustrative microcontroller 50. If more PWM outputs were available on microcontroller 50, transmitter 10 could include additional 4–20 mA output loops without the power consumption of digital isolator 54 affecting the output signals.

In addition, having the loop isolation within transmitter 10 allows the multiple loops to be powered by the same power supply and allows for the output loops to be connected to a single common ground at the power supply. If the grounds of the output loops were tied together without isolation, the 4–20 mA signals could interfere with one another and fail to function properly. Instead, isolation of the 4–20 mA loop control circuits in transmitter 10 allows for the use of the common ground at the power source for the output loops at the power supply without affecting the 4–20 mA output signals.

Although the invention has been described in detail with reference to a certain preferred embodiment, variations and modifications exist within the scope and spirit of the present invention as described and defined in the following claims.

We claim:

1. A measuring transmitter assembly using the same lines for power input and for output signals and a single power supply, the measuring transmitter comprising
   a first power input and signal output loop coupled to the power supply,
   a second power input and signal output loop coupled to the power supply,
   a first sensor for providing a first input signal in response to the value of a first parameter,
   a second sensor providing a second input signal in response to the value of a second parameter, and
   a controller coupled to the first and second sensors and to the first and second power input and signal output loops, the controller providing a first output signal on the first power input and signal output in response to the first input signal and a second output signal on the second power input and signal output loop in response to both the first input signal and the second input signal.

2. The measuring transmitter assembly of claim 1, further comprising a third power input and signal output loop coupled to the power supply, a third sensor providing a third input signal in response to the value of a third parameter and the controller further provides a third output signal on the third power input and signal output loop in response to the third input signal.

3. The measuring transmitter assembly of claim 2, further comprising a fourth power input and signal output loop coupled to the power supply, a fourth sensor providing a fourth input signal in response to the value of a fourth parameter and the controller further provides a fourth output signal on the fourth power in out and signal output loop in response to the fourth input signal.

4. The measuring transmitter assembly of claim 1, wherein each of the first and second output signals are delivered on the first and second power input and signal output loops by first and second 4–20 milliampere loop control circuit to have output current levels between 4 and 20 milliamps.

5. The measuring transmitter assembly of claim 1, further comprising a digital isolator electrically isolating the first and second power input and signal output loops.

6. The measuring transmitter assembly of claim 1, further comprising a calibration switch capable of being set to one of a plurality of different positions that each represent a different calibration signal, a calibration signal being provided in response to a selected position of the calibration switch, the controller receiving the chosen calibration signal and providing the first and second output signals in response to the calibration signal and the first and second input signals.

7. A measuring transmitter assembly using the same lines for power input and for output signals and a single power supply, the measuring transmitter comprising
   a first power input and signal output loop coupled to the power supply
   a second power input and signal output loop coupled to the power supply
   a first sensor for providing a first input signal in response to the value of a first parameter,
   a second sensor providing a second input signal in response to the value of a second parameter,
   a controller coupled to the first and second sensors and to the first and second power input and output loops, the controller providing a first output signal in response to the first input signal and providing a second output signal in response to the second input signal, and,
   a digital isolator for electrically isolating the first power input and signal output loop from the second power input and signal output loop to eliminate interference between the first and second output signals.

8. The measuring transmitter assembly of claim 7, further comprising a third sensor providing a third input signal in response to the value of a third parameter and a fourth sensor providing a fourth input signal in response to the value of a fourth parameter, a third power input and signal output loop, a fourth power input and signal output loop, the controller further providing a third output signal in response to the third input signal and a fourth output signal in response to the fourth input signal, the third and fourth power input signal output loops being electrically isolated from one another and from the first and second power input and signal output loops by the digital isolator.

* * * * *